United States Patent [19]
Chen et al.

[11] Patent Number: 5,800,778
[45] Date of Patent: Sep. 1, 1998

[54] SEALANT FOR SAMPLE HOLDER

[75] Inventors: Patrick K. Chen, Chesterfield, Mo.; Raymond E. O'Bear, Granite City, Ill.

[73] Assignee: bioMérieux Vitek, Inc., Hazelwood, Mo.

[21] Appl. No.: 455,404

[22] Filed: May 31, 1995

[51] Int. Cl.⁶ .................................................. B01D 53/22
[52] U.S. Cl. ........................... 422/48; 422/102; 422/61
[58] Field of Search ................................ 422/56, 58, 61, 422/48, 102, 104, 99

[56] References Cited

U.S. PATENT DOCUMENTS

| | | |
|---|---|---|
| 3,963,355 | 6/1976 | Aldridge, Jr. et al. . |
| 4,038,151 | 7/1977 | Fadler et al. . |
| 4,116,775 | 9/1978 | Charles et al. . |
| 4,118,280 | 10/1978 | Charles et al. . |
| 4,318,994 | 3/1982 | Meyer et al. . |
| 4,883,641 | 11/1989 | Wicks et al. ............... 422/58 |
| 4,952,373 | 8/1990 | Sugarman et al. ........... 422/61 |
| 5,021,294 | 6/1991 | Karasawa et al. . |
| 5,219,762 | 6/1993 | Katamine et al. ........... 422/61 |
| 5,364,766 | 11/1994 | Mach et al. ................. 422/56 |
| 5,374,395 | 12/1994 | Robinson et al. . |

OTHER PUBLICATIONS

Derwent Publications Database WPI Section Ch, Week 9320 Class A92, AN93–164008 XP002013177 & JP 05 096690 A (Dainippon Printing Co.) Apr. 20, 1993 (two page document included in European Search Report).

European Search Report dated Sep. 17, 1996 from European Patent Application No. 96303458.

L.C. Lopez et al., "Synthesis, Structure, and Properties of Poly (4–Methyl–1–pentene)" J.M.S.–Rev. Macromol, Chem. Phys. C32 (3 & 4), 301–406 (1992).

*Primary Examiner*—Lyle A. Alexander
*Attorney, Agent, or Firm*—McDonnell Boehnen Hulbert & Berghoff

[57] ABSTRACT

An improved sealant for a biocard or other sample holder is provided. The sealant achieves low weight, good tensile strength, and high oxygen permeability while avoiding excessive fluid evaporation, speeding incubation times.

17 Claims, 18 Drawing Sheets

FIG.1
FIG.2
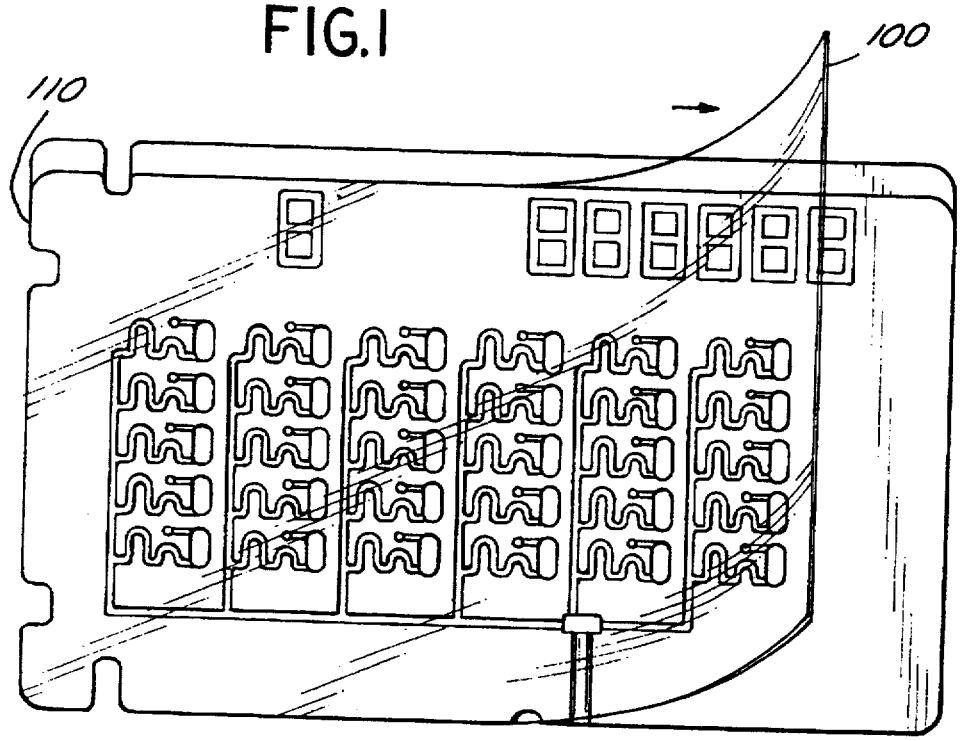

FIG. 3

UNITS OF MEASURE: SCC/100 IN²/24 HOURS / 25°C

| MATERIAL | POINT THICKNESS TESTED | O₂ TRANSMISSIBILITY (TEST VALUE) | O₂ PERMEABILITY RELATIVE VALUE (1.0 MIL) |
|---|---|---|---|
| PET (MYLAR) | 1.0 MIL | 3.9 | 3.9 |
| FEP | 1.75 MIL | 529 | 926 |
| PFA | 2.0 MIL | 710 | 1419 |
| TPX | 2.0 MIL | 2452 | 4903 |
| BOPP | 1.0 MIL | 150 | 150 |
| POLYSTYRENE | 1.0 MIL | 290 | 290 |

FIG.14 MEAN PERCENT CHANGE VS. TIME
II-FLAVOBACTERIUM ODORATUM

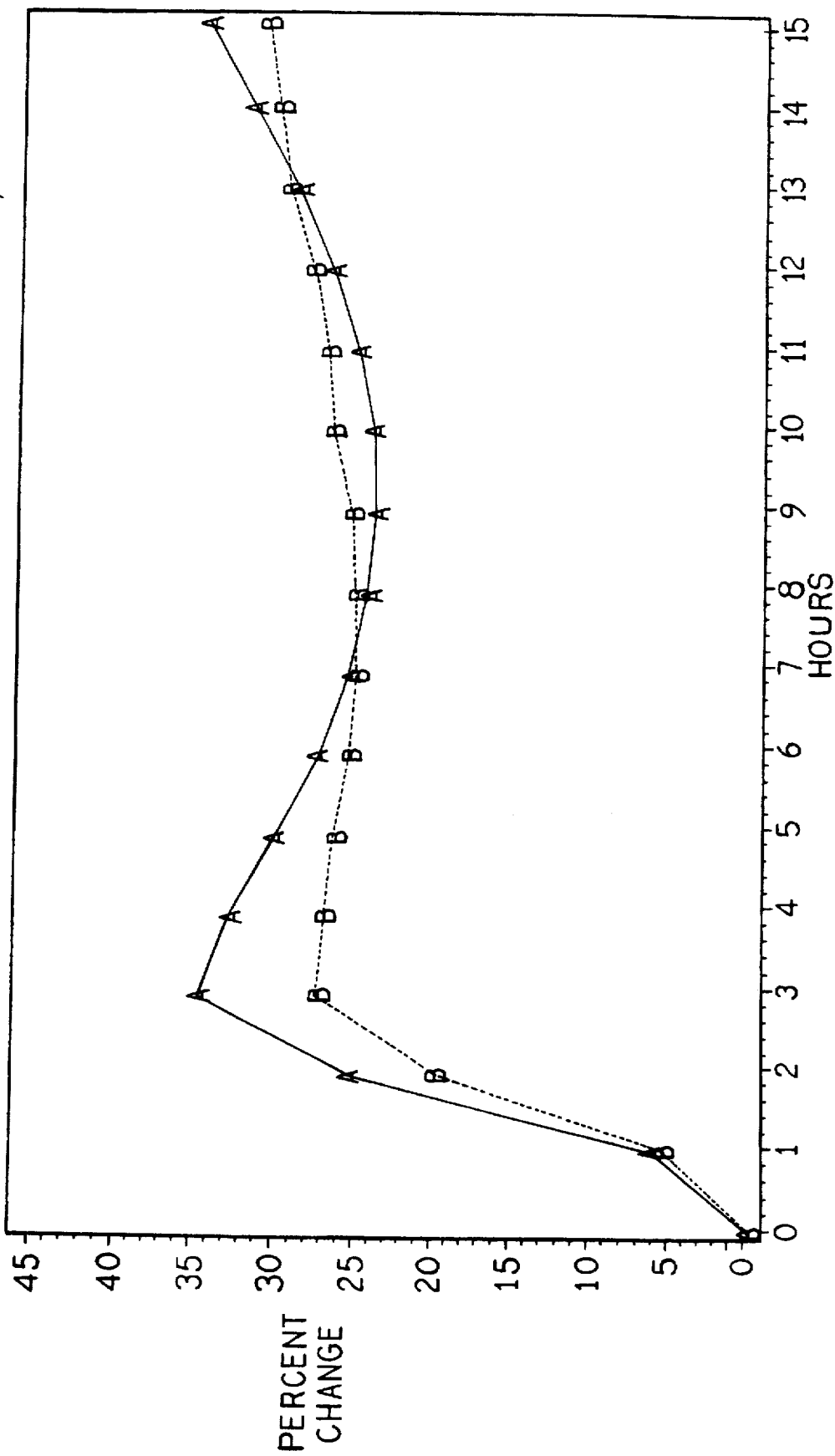

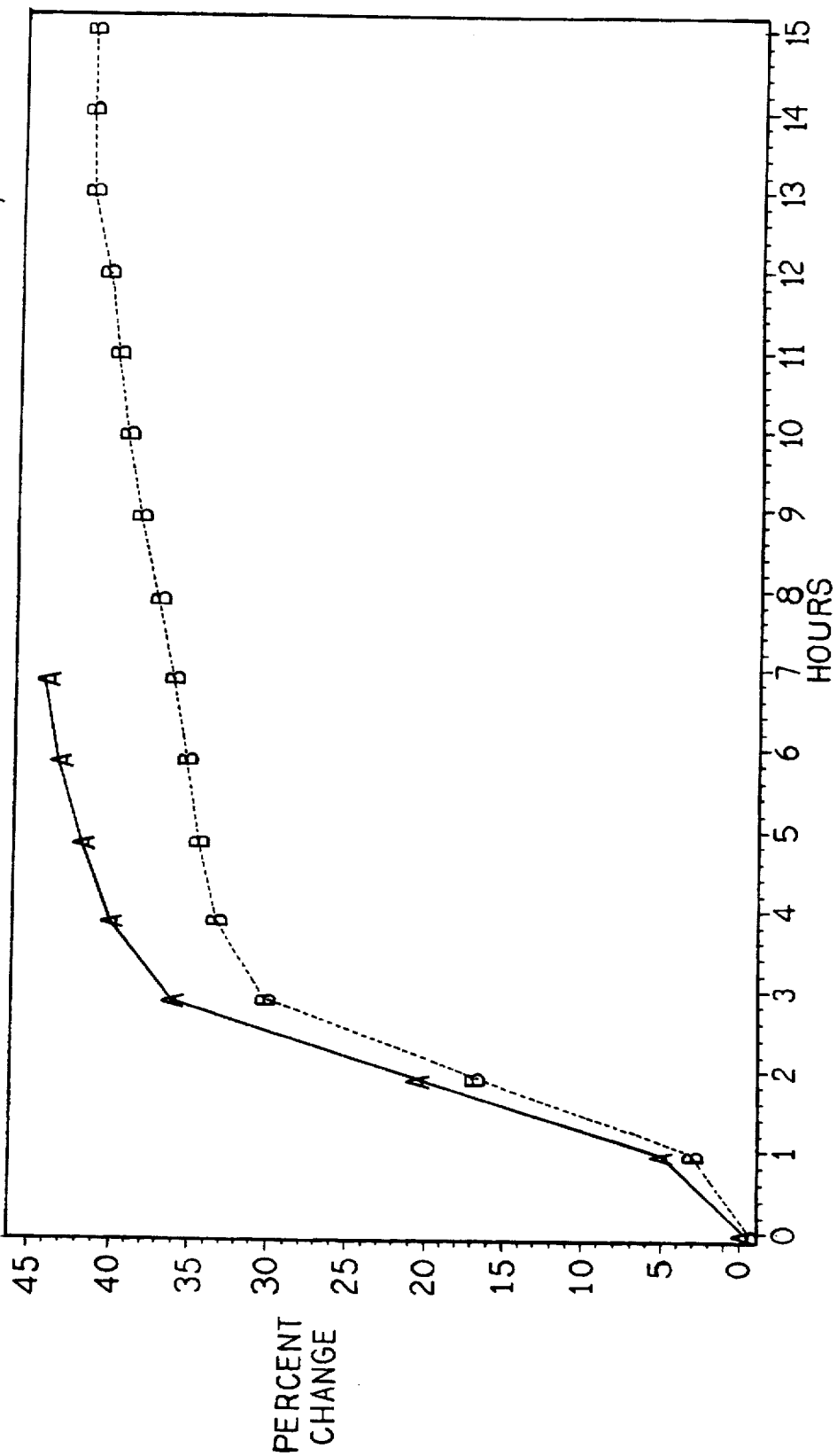

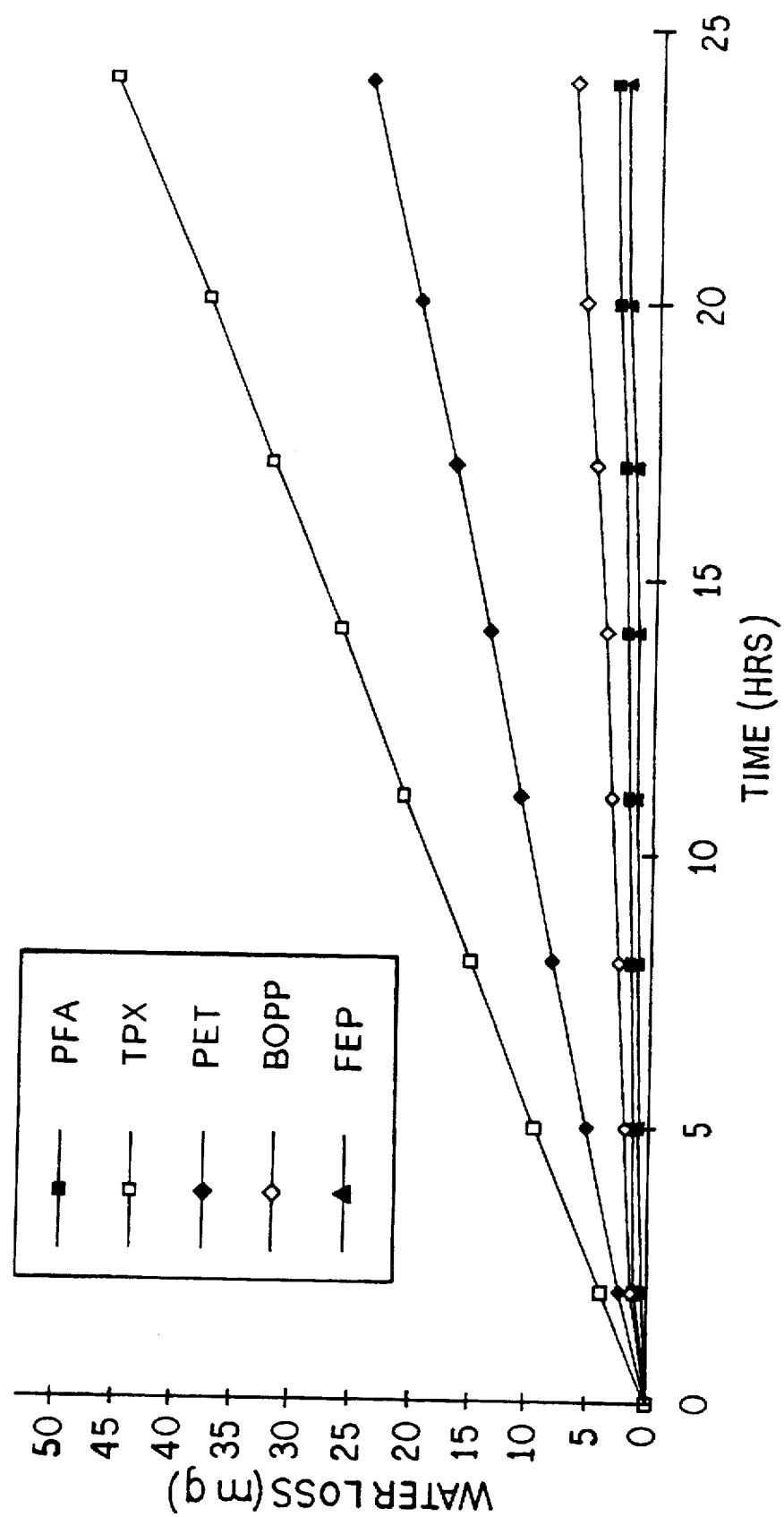

SEALANT FOR SAMPLE HOLDER

FIELD OF THE INVENTION

The invention relates to an improved sealant for biocards and other sample holders used for analyzing biological samples, and other applications.

BACKGROUND OF THE INVENTION

Biocards have been used to hold samples of blood or other biological samples in a spectroscopic or other automated reading machine. In such machines, a small biocard, roughly the size of a playing card, receives biological samples. The card typically holds the samples in a series of small wells, formed in the card in rows and columns.

The wells of the cards are filled with appropriate reactants, which are typically dried in place. The card and reactant are then sealed tightly in some manner, typically by adhesive tape on both sides. Later the card receives a biological sample, which mixes with the reactant and may be placed under incubating conditions so that the biological agent that may be present in the sample is permitted to grow. The biological sample may be a direct patient sample, or patient material which is diluted or otherwise treated for analysis.

After incubation, the samples contained in the wells are placed in front of a laser, fluorescent light or other illumination source. The content of the sample in a given well can then be deduced according to readings on the spectrum or other characteristics of the transmitted or reflected radiation. Biocards of this general type for use in these biochemical applications can for example be seen in U.S. Pat. Nos. 4,318,994, 4,038,151 and others.

Despite the general success of biocards in this application, there is an ongoing desire to improved the performance of the incubation process and readings on card samples. One significant aspect of the process is the way that the reactant and treated sample is sealed into the card. This is typically done using adhesive tapes made of conventional materials, such as PFA and FEP (which are polyfluorinated polymer films), PET and BOPP. While materials like that have performed satisfactorily in biological sample implementations, there is an ongoing desire to make the seal, integrity and efficiency of the incubation and process greater and reliable.

SUMMARY OF THE INVENTION

It is accordingly an object of the invention to provide an improved sealant for biocards and other applications.

It is another object of the invention to provide an improved sealant for a biocard which fosters incubation efficiency.

It is another object of the invention to provide an improved sealant for a biocard with superior oxygen permeability.

It is another object of the invention to provide an improved sealant for a biocard with good transparency for illumination of the sample.

The invention achieving these and other objects is a sealant for use in biocards or other analytic applications, having significantly improved incubation properties. The sealant of the invention is an optically clear material made from polymethylpentene, to which adhesive is applied for sealing the facing surfaces of the card with reliability, yet low weight and high oxygen permeability.

BRIEF DESCRIPTION OF THE DRAWINGS

The invention will be described with reference to the drawings, in which like parts are labelled with like numbers. The drawings are briefly described below.

FIG. 1 illustrates a front view of a biocard, and application of an improved sealant according to the invention, to the front of the card.

FIG. 2 illustrates a side view of the biocard of FIG. 1.

FIG. 3 illustrates a chart of the characteristics for the sealant according to the invention and other sealant tapes, including oxygen transmissibility and permeability.

FIG. 4–18 each illustrate a chart of the growth pattern of various biological agents sealed in a card using the improved sealant of the invention, and conventional tapes.

FIG. 19 illustrates a chart of evaporative characteristics for the improved sealant of the invention, and conventional tapes.

DETAILED DESCRIPTION OF THE DRAWINGS

Figure 4:
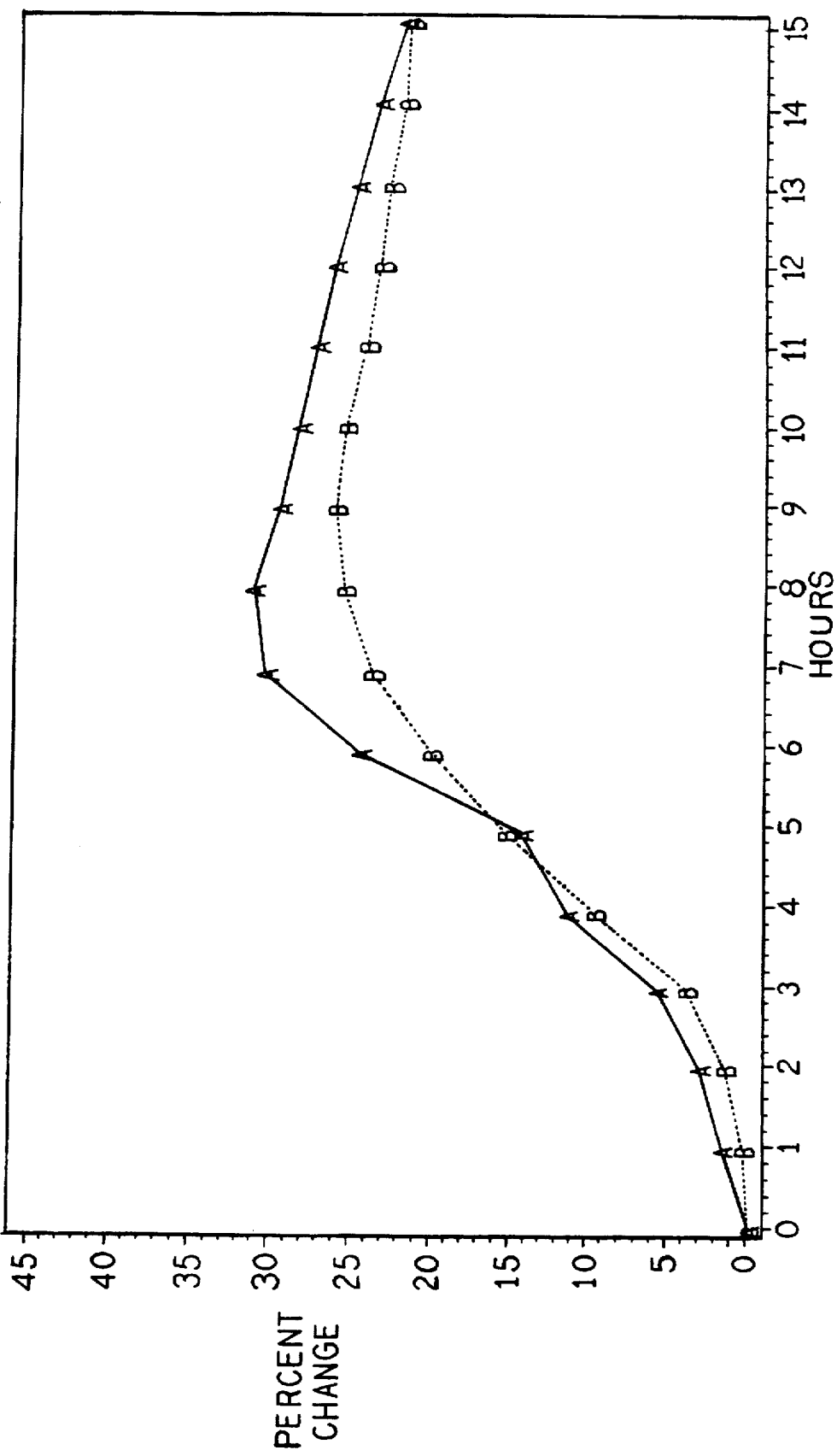
Figure 5:
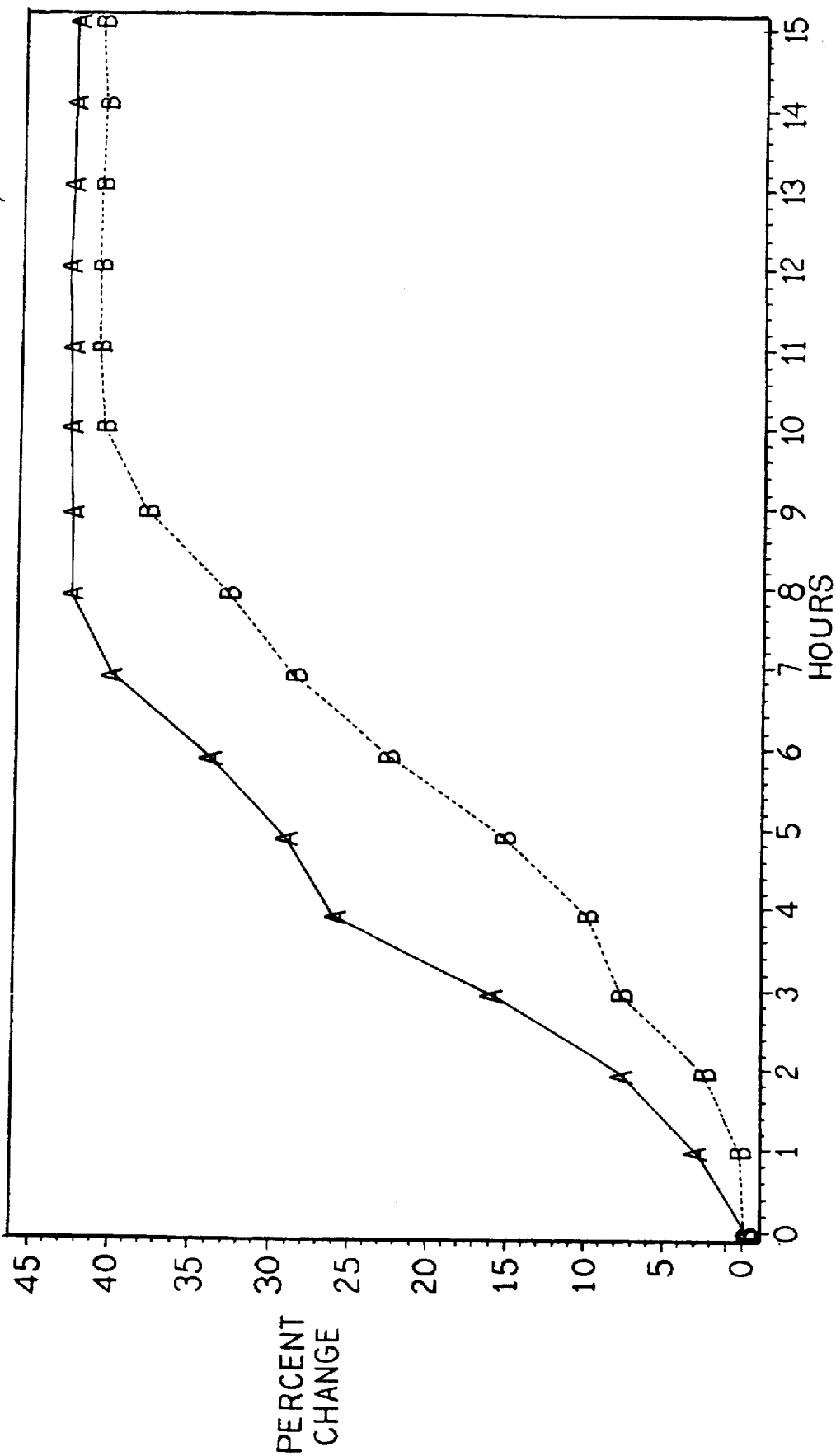
Figure 6:
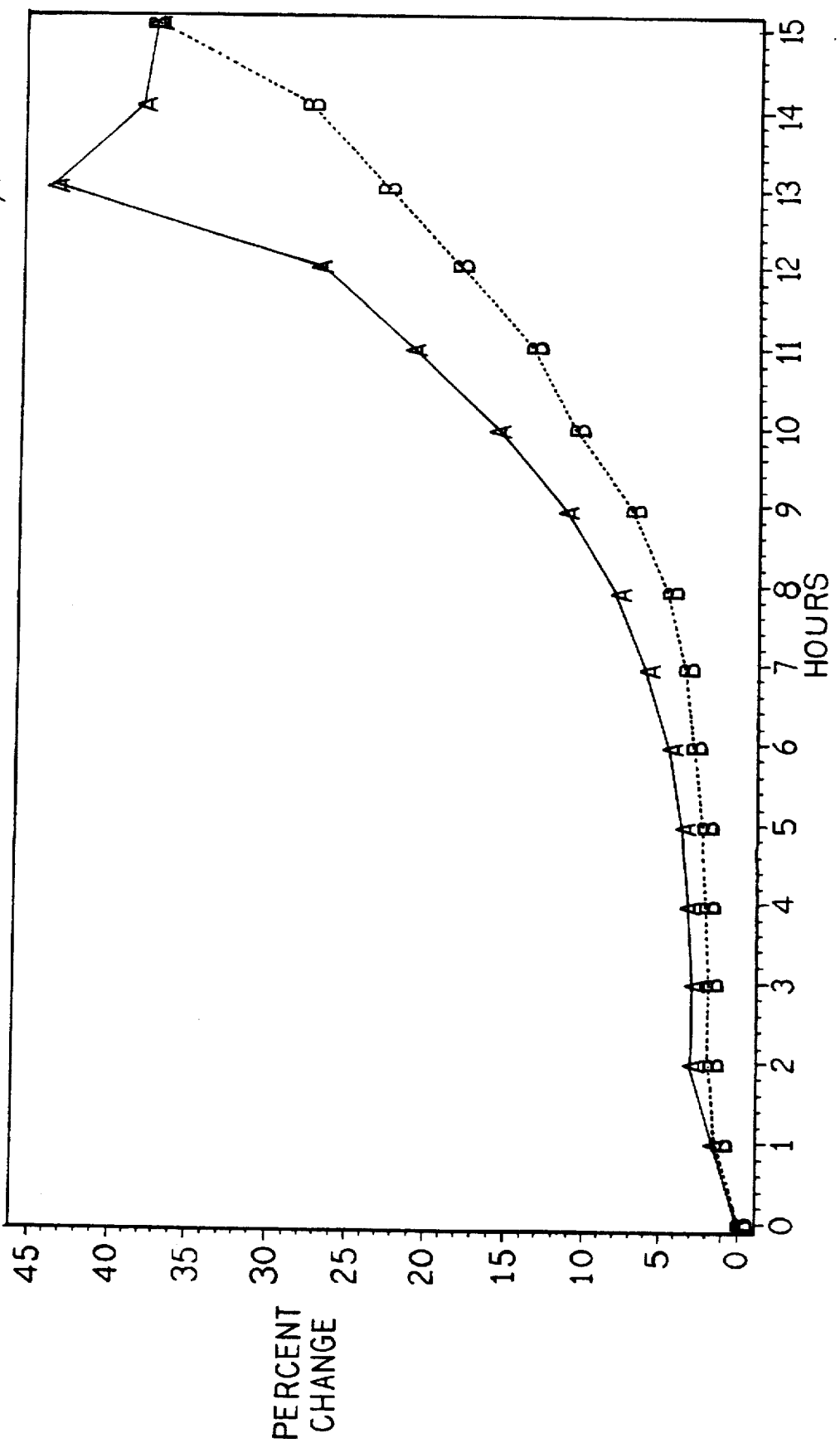
Figure 7:
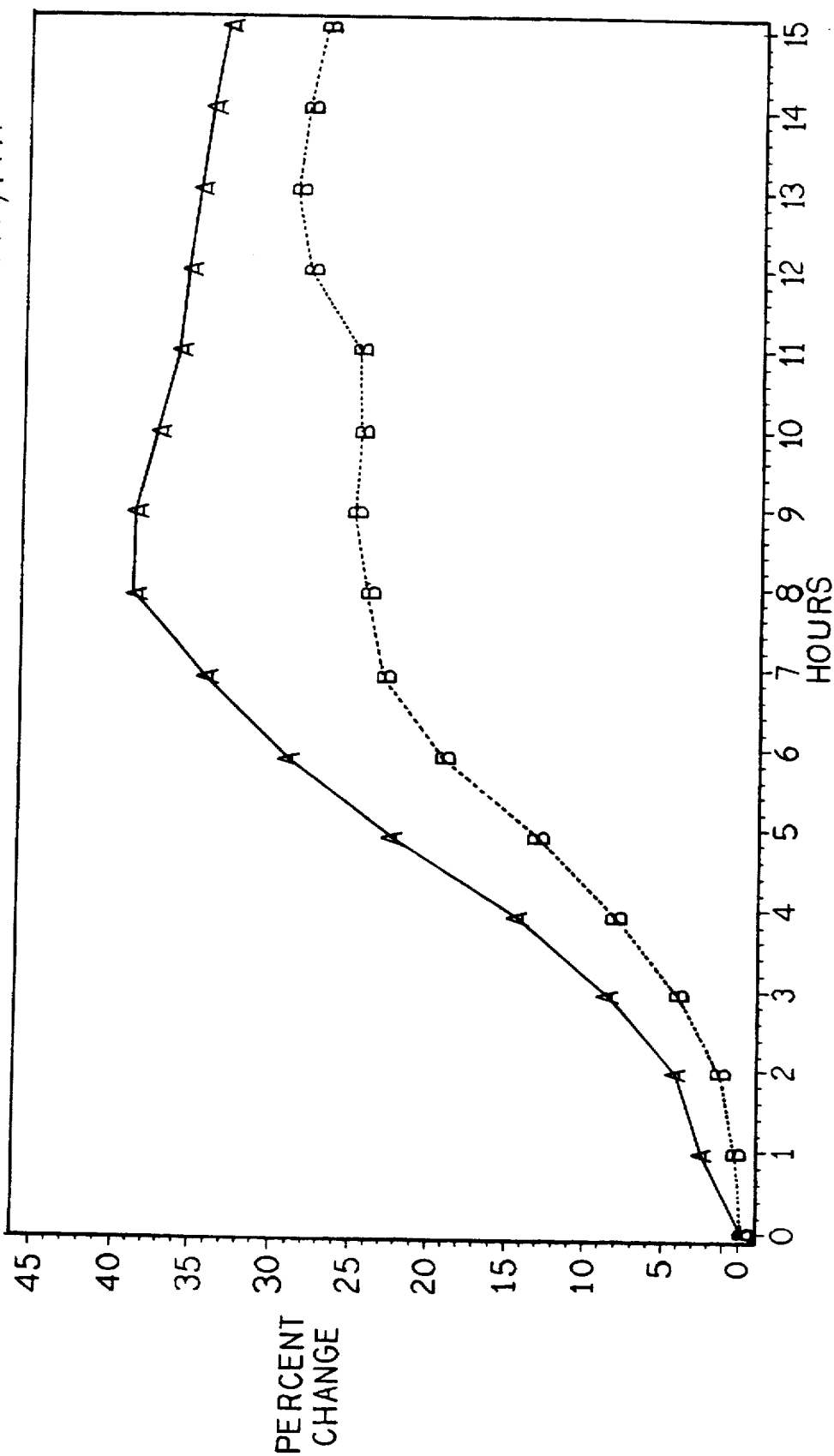
Figure 8:
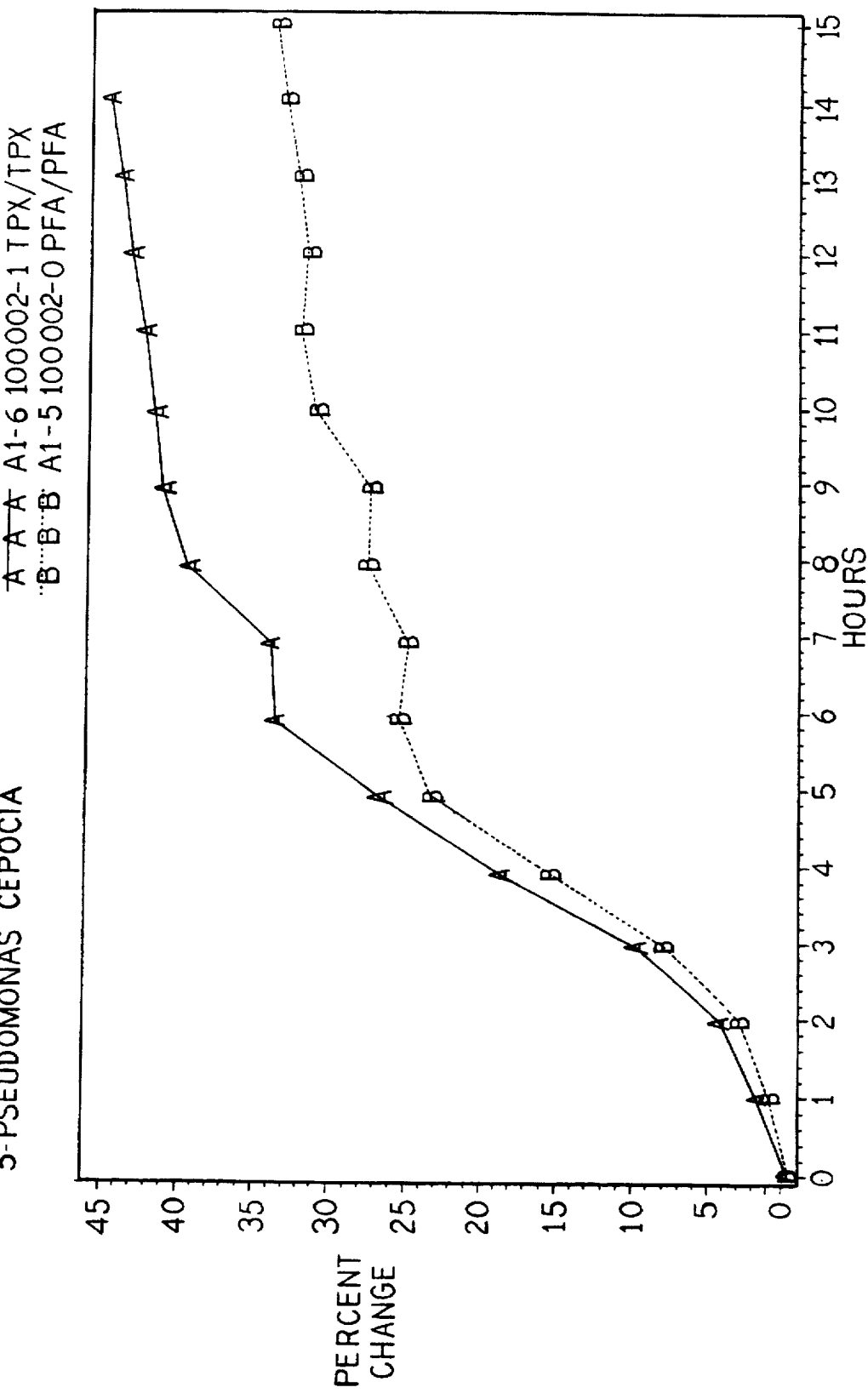
Figure 9:
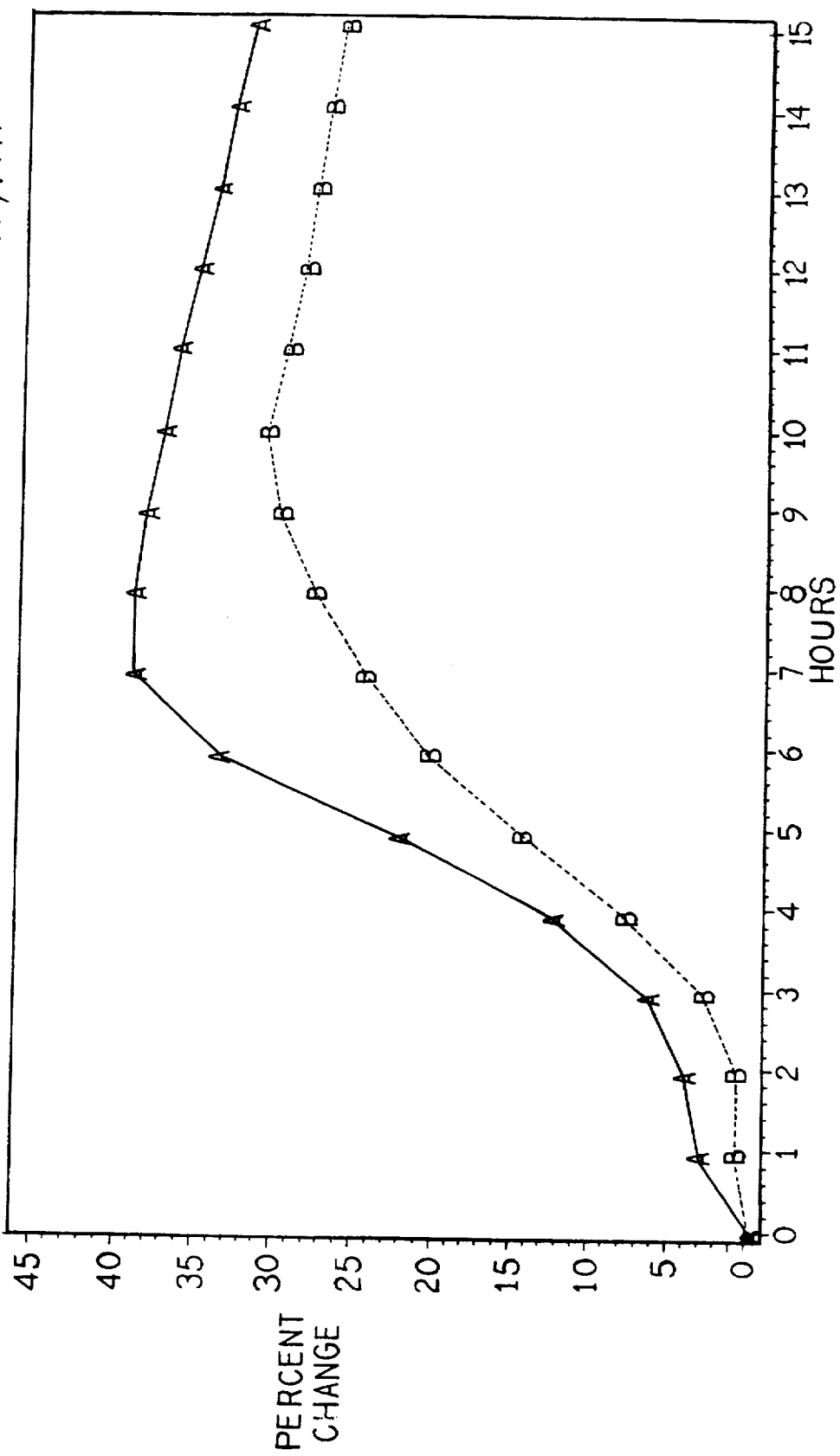
Figure 10:
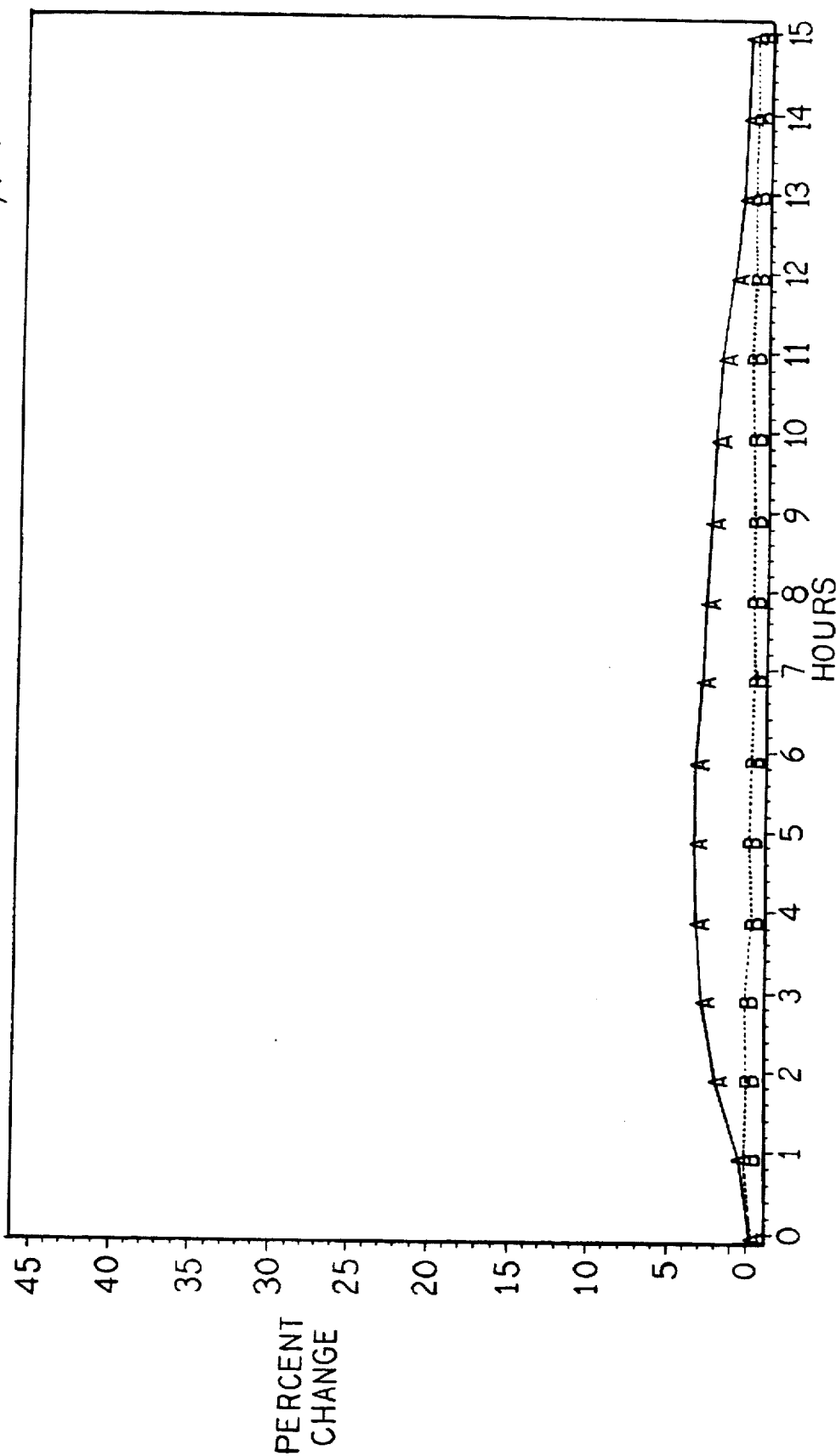
Figure 11:
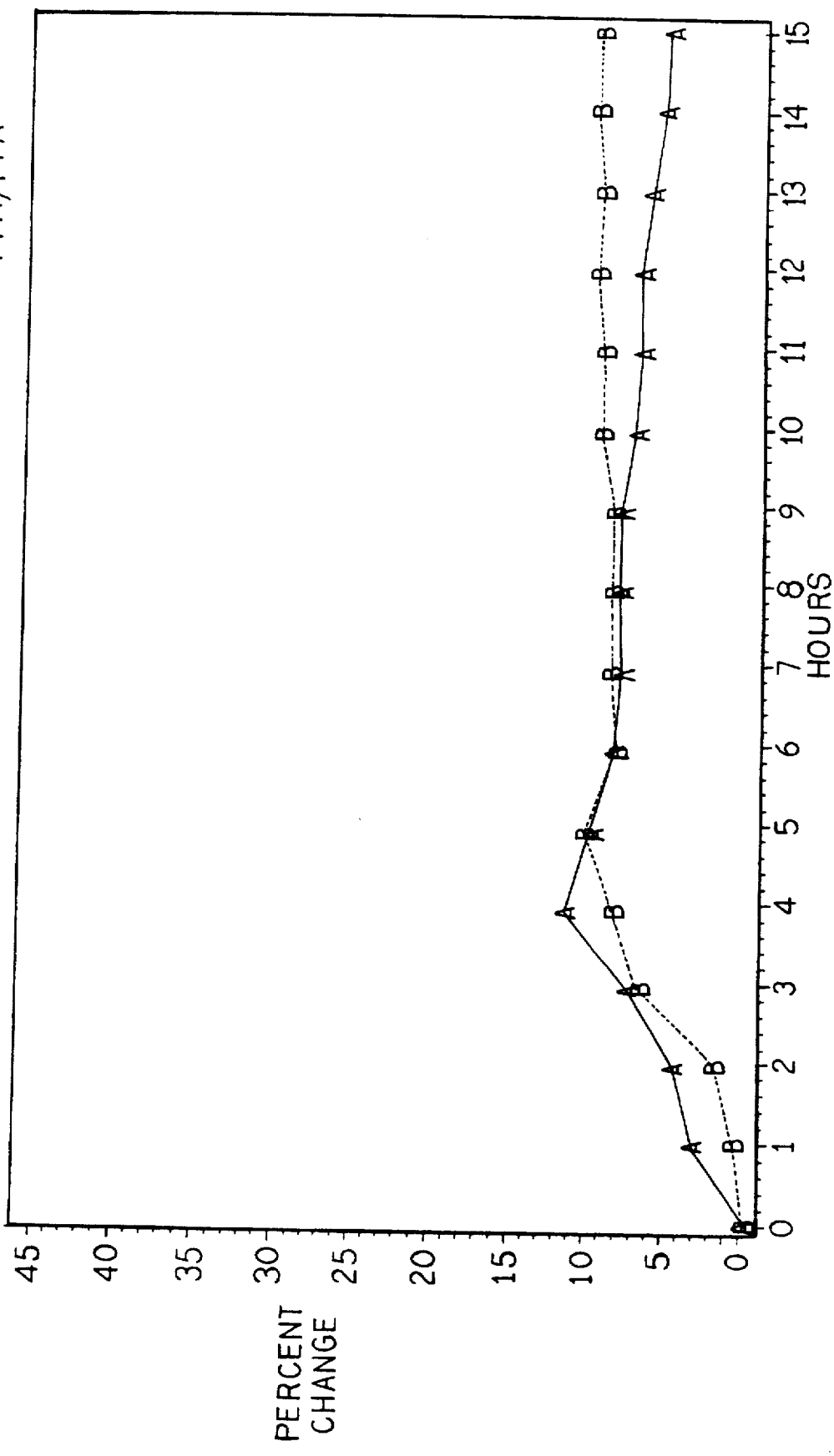
Figure 12:
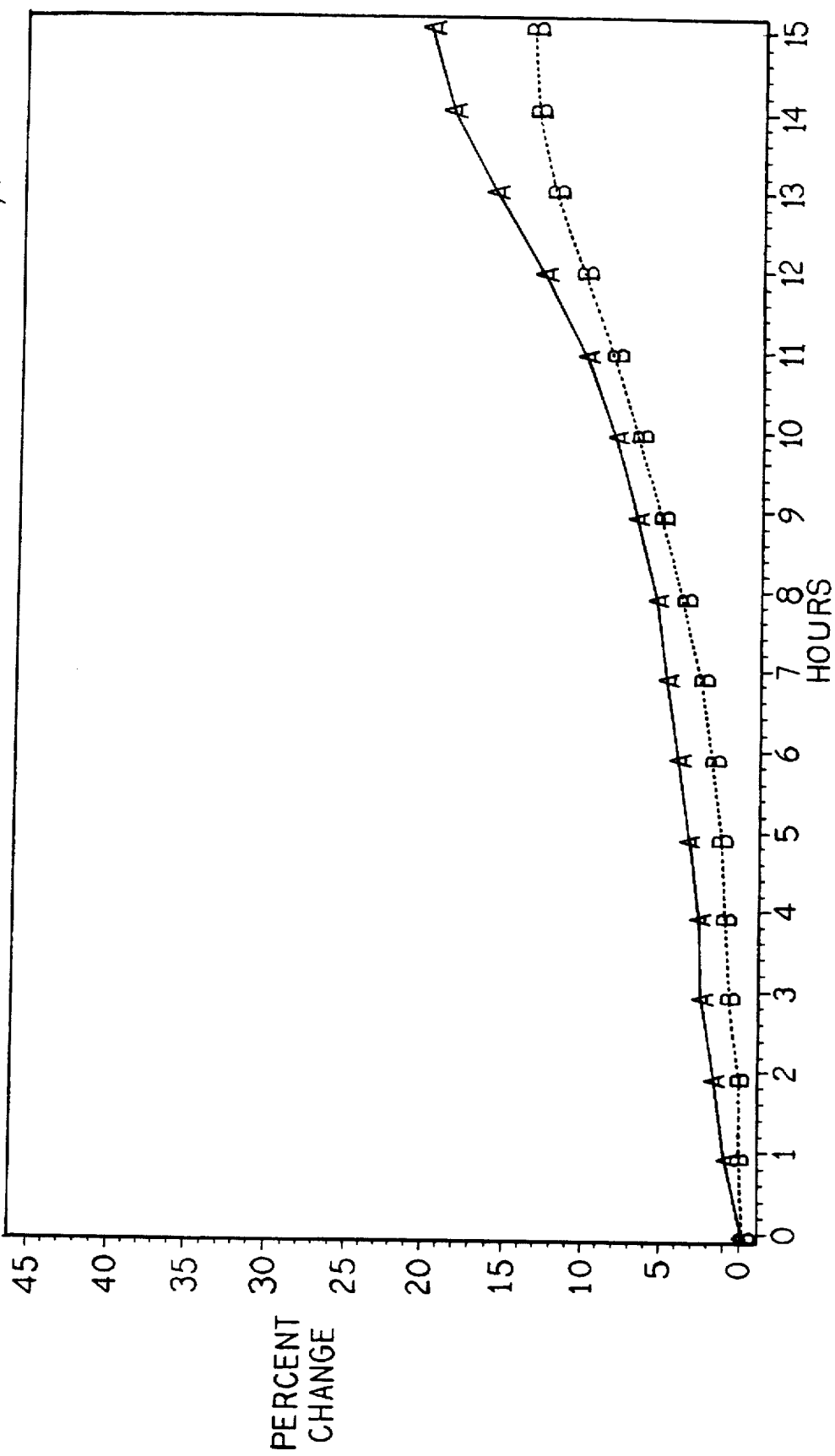
Figure 13:
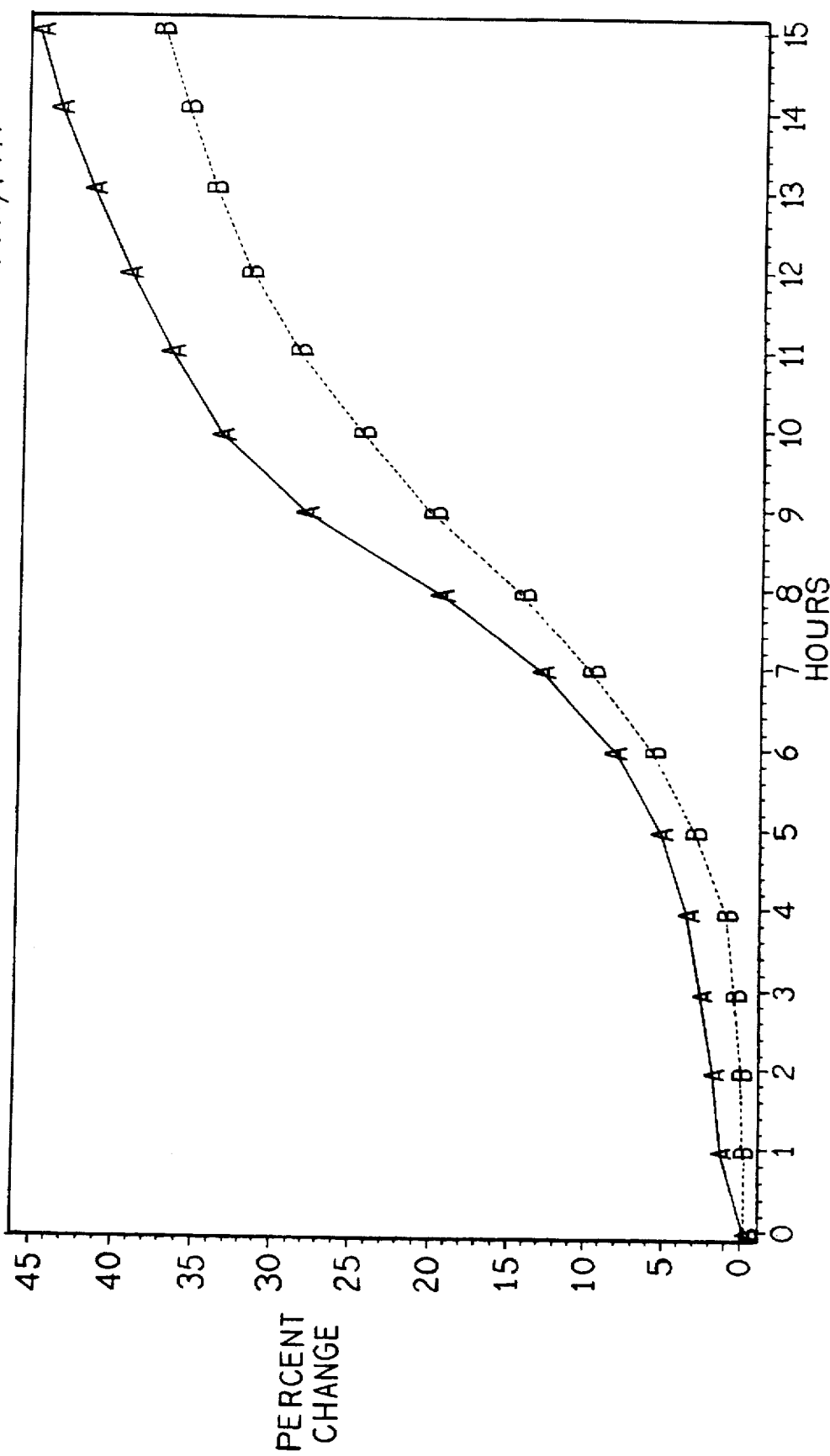
Figure 14:
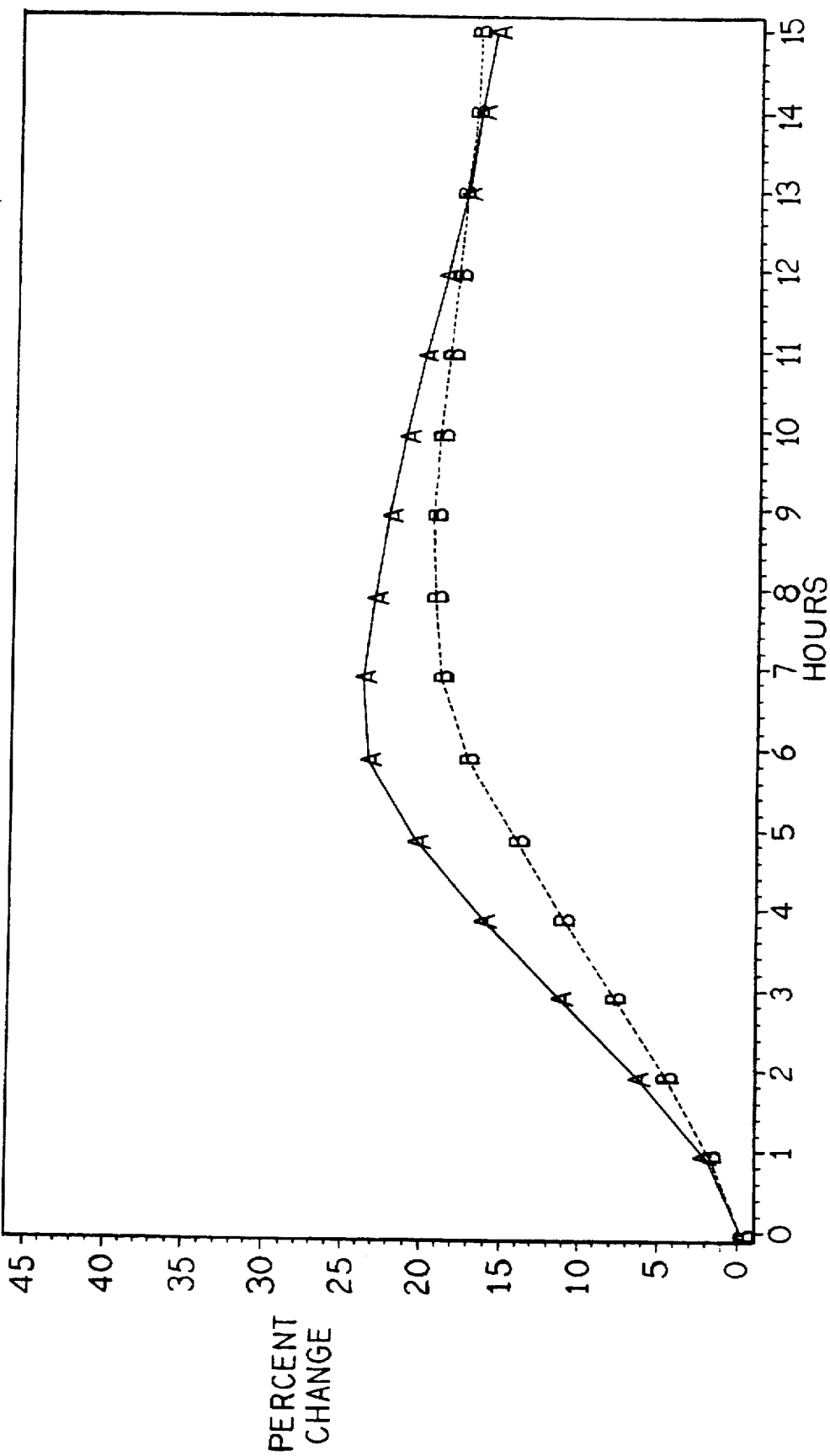
Figure 15:
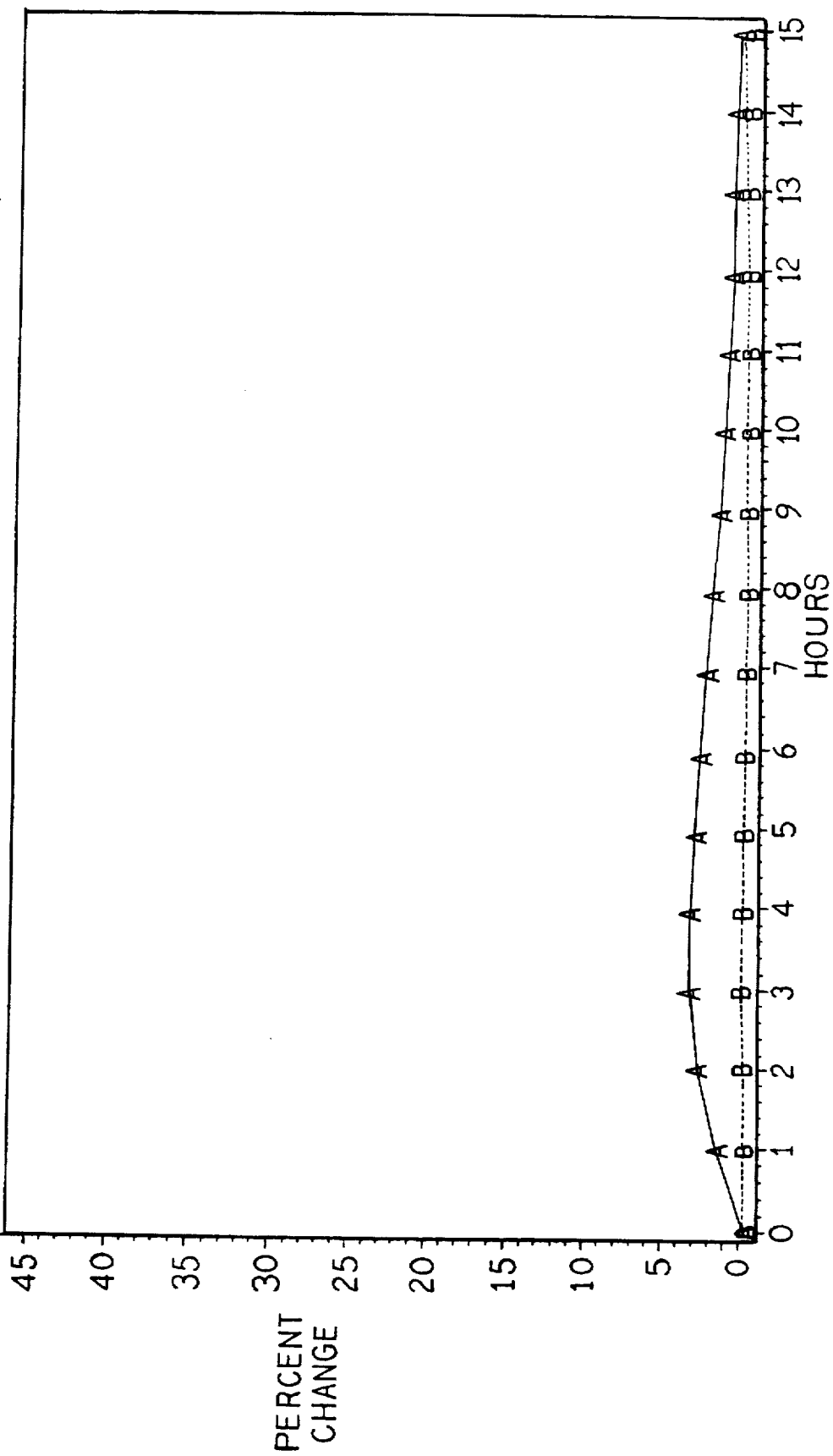
Figure 16:
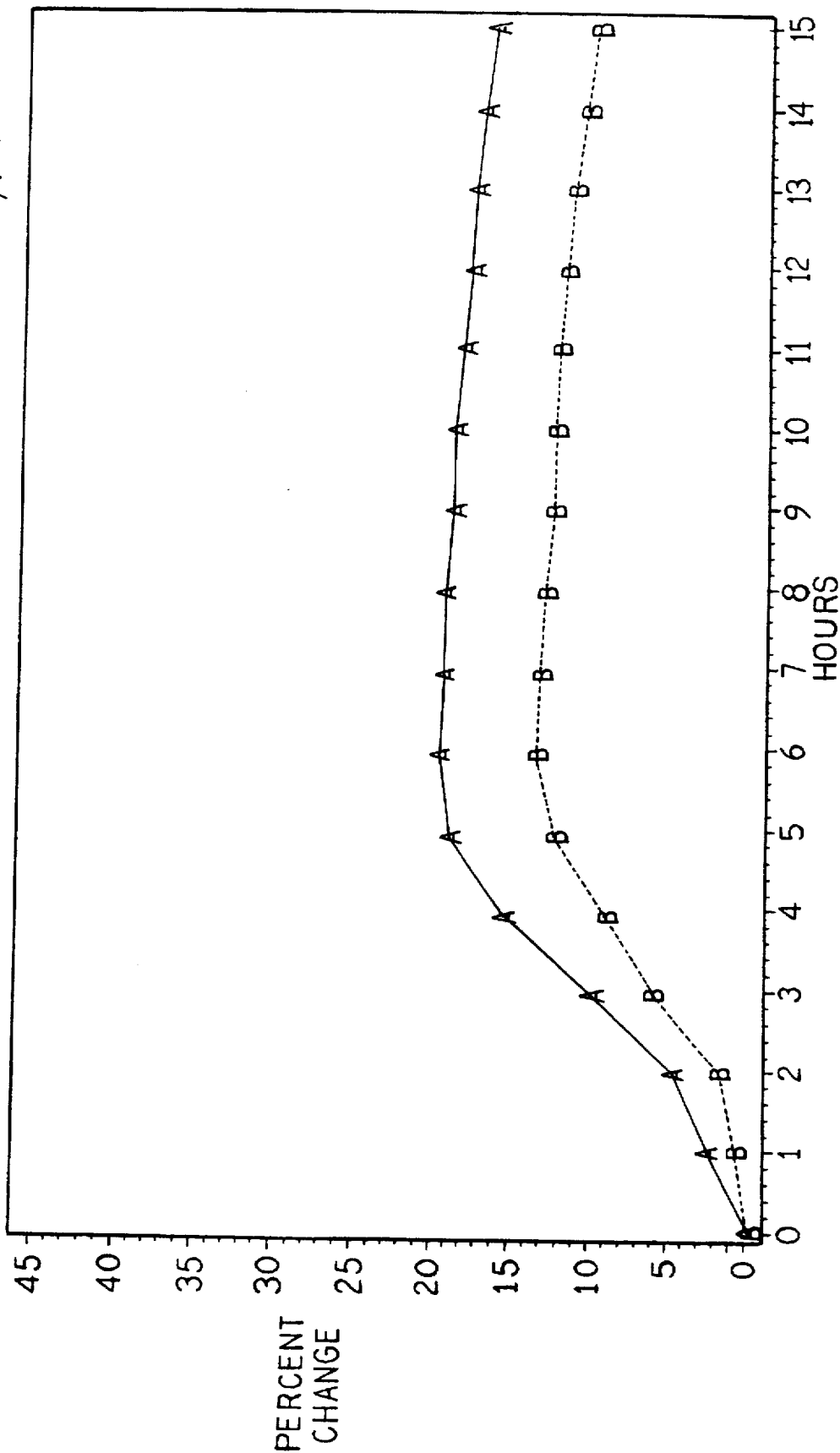

The invention is illustrated and characteristics shown in the context of FIGS. 1–19. This embodiment provides an improved sealant 100 illustrated in FIG. 1 in application to a biocard 110, generally in the form of adhesive-backed plastic film or membrane which can be rolled, measured, cut and otherwise easily handled when sealing reactants and samples into biocards or other sample holders. Any suitable adhesive backing, in laminate or other form, can be employed in the improved sealant of the invention. The sealant 100 is typically applied to both the front surface and rear surface of the biocard (or other sample holder), to seal the card wells which pass through the card as apertures, but could be applied to one or another side, depending on the application and sample holder used.

The sealant 100 of the invention is developed from a particular form of material. That material is polymethylpentene (PMP), known commercially as "TPX", and available from the Phillips and Mitsui companies. The material has been known for some time, for instance in solid plastic and sheet form. However, while PMP has been used in applications such as lining electronic circuit boards, metal casting molds for airplanes and other parts, the material has not been used as a sealant for biological or other sample analysis. General discussion of polymethylpentene as a material may be found in L. C. Lopez, G. L. Wilkes, P. M. Stricklen and S. A. White, "Synthesis, Structure, and Properties of Poly (4-Methyl-1-pentene)", J.M.S.-Rev. Macromol. Chem. Phys., C32(3&4), 301–406 (1992).

The inventors have discovered however that PMP material, in film form, possesses a unique combination of properties that make it particularly effective as a biocard sealant. In tape form, generally 1.2 mile thick, PMP exhibits good tensile strength, good handleability, excellent clarity and very light weight (having a density of approximately 0.8 g/cubic cm). These properties all lend themselves to a particularly suitable sealant on biocards, and other applications. FIG. 3 shows a table of the oxygen transmissibility and permeability of a sample card having a polymethylpentene membrane in accordance with the invention (item TPX in the table) as compared to other sealant films, including mylar (PET), FEP, and polystyrene. Note that the oxygen transmissibility is markedly improved over the other films, at least by a factor of three over the next closest film, PFA. Note also that the oxygen permeability is also increased by at least a factor of 3.

However, an improved sealant incorporating PMP provides not only these, but the separate and significant advantage that the tape has much improved oxygen permeability, in the range of 4800–5000 cc/100 in²/24 hours/25° C./ at 2 mil thickness. This is a marked advantage in the incubation of the microorganism contained in the biological sample, since by and large the microorganisms in the biological samples respond favorably, with increased growth rates, in an enhanced oxygen environment. The biological sample so developed may be a direct sample from the patient, or be patient sample which is extracted, diluted, suspended, or otherwise treated, in solution or otherwise.

FIGS. 4–18 for example illustrate test incubations using a sampling of different biological pathogens, largely gram-negative (Gram staining technique) bacteria. The rate of growth in most illustrated segments in most time periods is significantly greater for the improved sealant of the invention, employing PMP film, than for conventional sealants as indicated. (The growth lines shown in the graphs are on a log scale). This effect is of course related to the oxygen permeability of the improved sealant of the invention.

Because the microorganism contained in the biological sample can be made to grow more quickly when sealed with the sealant 100 of the invention, more samples can be processed on a given automated reading machine in a given amount of time. It may be noted that the improved sealant of the invention has oxygen permeability of approximately 4 to 6 times that of conventional FEP and PFA films, so the bacterial or other growth environment within the wells is oxygen-rich compared to known sealing technology.

While the improved sealant of the invention has the property of superior oxygen permeability, it at the same time possess adequate resistance to evaporation such that the samples lodged in the wells will not dry up during the relatively shortened incubation. The evaporative properties are for example illustrated in FIG. 19, in which it can be seen that the rate of water loss for PMP sealant according to the invention exceeds that of other conventional tapes. However, the inventors have determined that the water-retention properties of the sealant 100 of the invention are still adequate to the application of biological analysis.

In addition, once the incubation period is over, the good optical transparency of the sealant permits accurate fluorescent, scattering, spectroscopic or other readings of each well, because the sealant is transparent to radiation. Little reflection, absorption of other optical interference occurs, contributing to better readings.

Because the improved sealant of the invention balances good strength, handleability, light weight and excellent oxygen permeability and transparency with sufficient water-retention properties, it significantly enhances the incubation phase of biocard reading and permits quicker more reliable readings.

The foregoing description of the improved sealant for a biocard of the invention is illustrative, and variations on certain aspects of the invention will occur to persons skilled in the art. It is for instance possible to apply the improved sealant of the invention to analytic procedures which are not necessarily biological, but still benefit from the blend of properties that the inventive sealant affords. The scope of the invention is accordingly intended to be limited only by the following claims.

We claim:

1. An apparatus for use in biological sample testing comprising:

a test sample card having a card body, said card body defining a well for receiving a fluid sample containing a microbiological agent and a reagent for said fluid sample;

a high oxygen transmissible and permeable membrane applied to said card body in a manner to cover said well and provide a high oxygen transmissible and permeable barrier between said microbiological agent and reagent in said well and an atmosphere external of said test sample card, said membrane being substantially impermeable to liquids and making an engagement to said test sample card, said membrane comprising polymethylpentene;

said high oxygen transmissible and permeable membrane permanently secured to said card body and covering said well in a manner so as to provide a closed reaction chamber for said microbiological agent and said reagent within said well, whereby said high oxygen transmissible and permeable membrane promotes the reaction between said reagent and said microbiological agent.

2. The apparatus according to claim 1, further comprising:

an adhesive backing for fixing the high oxygen transmissible and permeable membrane to said card body of the test sample card.

3. The apparatus according to claim 1, wherein the high oxygen transmissible and permeable membrane at a thickness of 2 mils has an oxygen permeability of 4800–5000 (cc/100 in²/24 hours/25° C.).

4. The apparatus of claim 1, wherein said reagent comprises a growth media for said microbiological agent.

5. The apparatus of claim 1, wherein said reagent comprises an antibiotic for said microbiological agent.

6. The apparatus according to claim 1, wherein the card body of said test sample card has a front surface and a rear surface, and said well defining an aperture through said card body between said front and rear surfaces.

7. The apparatus according to claim 6, wherein the test sample card comprises a plurality of sample wells arranged in an array, said high oxygen transmissible and permeable sealing membrane covering said array of sample wells.

8. A sample holder, comprising:

a sample holder body having at least one well and defining front and rear surfaces, and a high oxygen transmissible and permeable membrane covering said well so as to provide a high oxygen transmissible and permeable barrier between a microbiological agent and a reagent loaded in said well and an atmosphere external of said sample holder, said membrane being substantially impermeable to liquids and applied to said at least one of said front and rear surfaces, said membrane comprising polymethylpentene;

said high oxygen transmissible and permeable membrane permanently secured to said sample holder body and covering said well in a manner so as to provide a closed reaction chamber for said microbiological agent and said reagent within said well.

9. The sample holder of claim 8, wherein said high oxygen transmissible and permeable sealing membrane is applied to both said front and rear surfaces of said sample holder.

10. The sample holder of claim 8, wherein said high oxygen transmissible and permeable sealing membrane has a thickness of 2 mils.

11. A biological test sample card, comprising a card body defining a plurality of sample wells, and having front and rear surfaces, said wells comprising an aperture extending between said front and rear surfaces, a high oxygen transmissible and permeable membrane applied to a portion of said front and rear surfaces so as to cover said sample wells, wherein said membrane is substantially impermeable to liquids and wherein said membrane comprises polymethylpentene.

12. The biological test sample card of claim 11, wherein said wells are arranged in an array and are loaded with reactants, said polymethylpentene membrane increasing the transmissibility of oxygen into said wells.

13. The biological test sample card of claim 12, wherein said polymethylpentene membrane is applied to said front surface and to said rear surface of said card.

14. The biological test sample card of claim 13, wherein said polymethylpentene membrane has a thickness of 2 mils.

15. An improved biological test sample card for use in optical analysis of a biological fluid sample containing a microbiological agent, comprising:

a test sample card body having front and rear surfaces and a plurality of sample wells forming apertures therethrough arranged in an array, said plurality of sample wells receiving a reagent for said microbiological agent;

a first oxygen permeable membrane applied to said front surface of said card body and covering all of said apertures in said card body, said first membrane comprising polymethylpentene, said first membrane being substantially impermeable to liquids and increasing the transmissibility of oxygen into said plurality of sample wells; and a second membrane to said rear surface of said card body and covering all of said apertures in said card body;

said high oxygen transmissible and permeable membrane and said second membrane permanently secured to said card body and covering all of said apertures in said card body in a manner so as to provide a plurality of closed reaction chambers for said microbiological agent and said reagent.

16. The biological test sample card of claim 15, wherein said first membrane at a thickness of 2 mils have an oxygen permeability of 4800–5000 (cc/100 in$^2$/24 hours/25° C.).

17. The biological test sample card of claim 15, wherein said first and second membranes are adhesively attached to said front and rear surfaces of said test sample card body.

* * * * *